United States Patent
Balbinot et al.

(10) Patent No.: US 10,124,067 B2
(45) Date of Patent: Nov. 13, 2018

(54) CHG-COMPATIBLE COMPOSITION AND METHOD

(71) Applicant: Sage Products, LLC, Cary, IL (US)

(72) Inventors: Jodi M. Balbinot, Cary, IL (US); Arthur C. W. Georgalas, Warwick, NY (US)

(73) Assignee: Sage Products, LLC, Cary, IL (US)

( * ) Notice: Subject to any disclaimer, the term of this patent is extended or adjusted under 35 U.S.C. 154(b) by 0 days.

(21) Appl. No.: 15/486,920

(22) Filed: Apr. 13, 2017

(65) Prior Publication Data

US 2017/0296670 A1    Oct. 19, 2017

Related U.S. Application Data

(60) Provisional application No. 62/321,814, filed on Apr. 13, 2016, provisional application No. 62/464,643, filed on Feb. 28, 2017.

(51) Int. Cl.

| | | |
|---|---|---|
| *A61K 47/34* | (2017.01) | |
| *A61K 9/00* | (2006.01) | |
| *A61K 31/155* | (2006.01) | |
| *A61K 47/14* | (2017.01) | |
| *A61K 47/32* | (2006.01) | |
| *A61Q 19/00* | (2006.01) | |
| *A61Q 17/00* | (2006.01) | |

(52) U.S. Cl.
CPC ............ *A61K 47/34* (2013.01); *A61K 9/0014* (2013.01); *A61K 31/155* (2013.01); *A61K 47/14* (2013.01); *A61K 47/32* (2013.01); *A61Q 19/00* (2013.01); *A61K 2800/75* (2013.01); *A61Q 17/005* (2013.01)

(58) Field of Classification Search
CPC ...................................................... A61K 47/34
See application file for complete search history.

(56) References Cited

U.S. PATENT DOCUMENTS

| | | | |
|---|---|---|---|
| 6,383,505 B1 * | 5/2002 | Kaiser | A01N 47/44 424/405 |
| 8,642,665 B2 | 2/2014 | Craig et al. | |
| 9,095,393 B2 | 8/2015 | Schaus et al. | |
| 2014/0378550 A1 | 12/2014 | Grundhofer | |
| 2015/0073051 A1 | 3/2015 | Cohen et al. | |
| 2015/0182435 A1 | 7/2015 | Casugbo et al. | |
| 2015/0306055 A1 | 10/2015 | Percival et al. | |

FOREIGN PATENT DOCUMENTS

| | | |
|---|---|---|
| WO | 2000/48569 A1 | 8/2000 |
| WO | 2001/78657 A1 | 10/2001 |

OTHER PUBLICATIONS

International Search Report for Application No. PCT/US2017/027429 dated Jul. 26, 2017, 4 pages.
Ali and Yosipovitch, Skin pH: From Basic Science to Basic Skin Care, Review Article, Acta Derm Venereol 2013; 93: 261-267.
Ali and Yosipovitch, Supplementary material to article by S. M. Ali and G. Yosipovitch, Skin pH: From Basic Science to Basic Skin Care, Acta Derm Venereol 2013; 93.
Easysnap Technology S.r.l., Easysnap—The One Hand Opening Unit Dose, http://www.easysnap.com/, downloaded on Sep. 26, 2017, 4 pages.
Provon, photographs of bottle of Provon moisturizing hand & body lotion, on the market prior to Apr. 13, 2016, 5 pages.

* cited by examiner

*Primary Examiner* — Svetlana M Ivanova
(74) *Attorney, Agent, or Firm* — Howard & Howard Attorneys PLLC

(57) ABSTRACT

A composition for soothing irritation that does not diminish the efficacy of a topical antiseptic is disclosed. The composition comprises an emollient, an emulsifier, and a film-forming agent. Also, a method of soothing irritation without diminishing the efficacy of a topical antiseptic product comprises the steps of providing the topical antiseptic product comprising a cationic antiseptic agent, providing the composition, applying the topical antiseptic product to a target area on skin of a patient to coat the target area with the cationic antiseptic agent, and applying the composition to the coated target area.

8 Claims, No Drawings

CHG-COMPATIBLE COMPOSITION AND METHOD

RELATED APPLICATIONS

This application claims priority to and the benefit of U.S. Provisional Patent Application No. 62/321,814, filed on Apr. 13, 2016, and U.S. Provisional Patent Application No. 62/464,643, filed on Feb. 28, 2017, the entire contents of which are hereby incorporated by reference.

FIELD OF THE DISCLOSURE

This disclosure generally relates to a composition. More specifically, this disclosure relates to the composition, which may be applied to skin that has been treated with chlorhexidine. The disclosure also relates to a method regarding the same.

BACKGROUND

Microorganisms including multi-drug resistant organisms (MDROs), such as Methicillin-resistant *Staphylococcus aureus* (MRSA), Vancomycin-resistant Enterococci (VRE), and *Acinetobacter*, are responsible for difficult-to-treat infections in humans. Widespread use (and sometimes over-use and/or misuse) of antibiotics has resulted in an increase in MDRO infections. Because MDROs demonstrate greatly reduced vulnerability to antibiotics, specific measures are taken to reduce the likelihood of or to prevent infection, particularly in hospitalized people who are to undergo invasive procedures, who have comprised immune systems, and who have open wounds. In some cases, these preventative steps occur before the patient arrives at the site where the procedure is to take place.

One such measure is the topical application of chlorhexidine gluconate ("CHG"), a broad-spectrum, persistent antiseptic. A convenient and effective means of applying CHG to the skin is with the use of a topical wipe, but application may also be accomplished using a solution or mixture of CHG applied directly to the skin. Patients may apply CHG at home prior to a surgical procedure, for instance the night before surgery, and/or medical practitioners may apply CHG, for instance, in the preoperative preparation of patients.

Although CHG itself is not a skin irritant, it can be associated with skin irritation because the patient population that is most likely to need and/or use CHG usually has frail skin due to age, chronic health conditions, or long-term hospitalization. Some patients may also experience discomfort and irritation after applying CHG owing to friction generated during the application process. Patients experiencing irritation associated with application of CHG may wish to apply a lotion, balm, or composition to soothe and moisturize the skin. In many instances, however, the use of an additional skin treatment is counterproductive, as lotions often contain compounds or have chemical characteristics that chemically deactivate chlorhexidine on the surface of the skin.

It has been a challenge to develop a composition that may be applied topically to skin treated with CHG, such that CHG persists on the surface of the skin and retains its antiseptic properties after application of the composition.

SUMMARY OF THE DISCLOSURE

A composition for soothing irritation that does not diminish the efficacy of a topical antiseptic product is disclosed. The composition includes an emollient, an emulsifier, and a film-forming agent. A method of soothing irritation that does not diminish the efficacy of a topical antiseptic product is also disclosed. The method includes the steps of providing the topical antiseptic product comprising a cationic antiseptic agent in a concentration of from about 0.5 to about 8% by weight based on the total weight of the topical antiseptic product, providing the composition, applying the topical antiseptic product to a target area on the skin of a patient to coat the target area with the cationic antiseptic agent, and applying the composition to the coated target area.

DETAILED DESCRIPTION OF THE DISCLOSURE

A composition for soothing irritation that does not diminish the efficacy of a topical antiseptic product ("the antiseptic product") is disclosed. The composition comprises an emollient, an emulsifier, a film-forming agent, and, optionally, an anionic compound.

As used herein, the terms "substantially" and "about" mean "approximately but not necessarily equal to," and when used in the context of a numerical value or range set forth means a variation of ±20%, or less, of the numerical value. For example, a value differing by ±20%, ±15%, ±10%, ±5%, ±4%, ±3%, ±2%, ±1%, 0.5% or any value in the range between −20% and +20%, would satisfy the definition of "substantially" or "about."

The Composition:

The composition for soothing irritation that does not diminish the efficacy of a topical antiseptic product is disclosed. The composition includes an emollient, an emulsifier, and a film-forming agent, which are described, in turn, below.

As is set forth above, the composition includes at least one emollient. An emollient may also be known as a moisturizer and may have the effect of making the epidermis softer and more pliable. The emollient may be, by way of non-limiting example, petroleum-based oils, petrolatum, vegetable oils, mineral oils, lanolin and derivatives thereof, glycerol esters and derivatives thereof, fatty esters, propylene glycol esters and derivatives thereof, alkoxylated carboxylic acids, *Aloe vera*, fatty alcohols, alkyl methicones, alkyl dimethicones, phenyl silcones, alkyl trimethylsilanes, and combinations thereof. In certain embodiments, the emollient includes dimethicone and *aloe vera*. Of course, still other emollients are contemplated.

The emollient typically has an electrical charge property selected from non-ionic, amphoteric, and cationic. In one embodiment of the composition in accordance with the principles of the present disclosure, the emollient may be a nonionic emollient. In another embodiment of the composition in accordance with the principles of the present disclosure, the emollient may be amphoteric. In yet another embodiment of the composition in accordance with the principles of the present disclosure, the emollient may be cationic.

In one particular embodiment, the emollient includes isopropyl palmitate. In some such embodiments of the composition, the isopropyl palmitate is present in an amount of from about 0.01 to about 20.00, of from about 0.50 to about 17.50, of from about 1.00 to about 15.00, of from about 2.00 to about 12.50, of from about 2.00 to about 10.00, of from about 2.00 to about 8.00, of from about 2.50 to about 7.00, of from about 2.50 to about 5.00, of from about 3.00 to about 4.00, or of about 3.00% by weight based on the total weight of the composition. In various non-limiting embodiments, all values and ranges of values between the aforementioned values are hereby expressly contemplated.

In another embodiment, the emollient may be caprylic capric triglyceride. In some such embodiments of the composition, the caprylic capric triglyceride is present in an amount of from about 0.01 to about 20.00, of from about 0.50 to about 17.50, of from about 1.00 to about 15.00, of from about 2.00 to about 12.50, of from about 2.00 to about 10.00, of from about 2.00 to about 8.00, of from about 2.50 to about 7.00, of from about 2.50 to about 5.00, of from about 3.00 to about 4.00, or of about 3.00% by weight based on the total weight of the composition. In various non-limiting embodiments, all values and ranges of values between the aforementioned values are hereby expressly contemplated.

In some embodiments, the composition may contain both isopropyl palmitate and caprylic capric triglyceride as emollients. In one embodiment, the composition contains both caprylic capric triglyceride and isopropyl palmitate at about 3.00% weight-to-weight.

Other specific emollients that may be used in a composition in accordance with the principles of the present disclosure, in similar percentage ranges to those listed above, include isopropyl mystirate, petrolatum, mineral oil, polypropylene glycol 15 (PPG-15), stearyl ether, lanolin oil, sunflower seed oil glyceride, glyceryl myristate, ethylhexyl palmitate, and myristyl myristate, among others.

In many embodiments, the emollient is present in the composition in an amount of from about 0.01 to about 20.00, of from about 0.50 to about 17.50, of from about 1.00 to about 15.00, of from about 2.00 to about 12.50, of from about 2.00 to about 10.00, of from about 2.00 to about 8.00, of from about 2.50 to about 7.00, or of from about 2.50 to about 5.00, % by weight based on the total weight of the composition. The amount of the emollient may vary outside of the ranges above, but is typically both whole and fractional values within these ranges. Further, it is to be appreciated that more than one emollient may be included in the composition, in which case the total amount of all the emollients included is within the above ranges. In various non-limiting embodiments, all values and ranges of values between the aforementioned values are hereby expressly contemplated.

As is set forth above, the composition includes at least one emulsifier. An emulsifier is a compound that assists in keeping the multiple phases of a composition mixed. For example, the oil phase of a composition would separate from the aqueous phase of the composition without the presence of at least one emulsifier. In one embodiment of a composition in accordance with the principles of the present disclosure, the emulsifier may be a nonionic emulsifier. In one particular embodiment, the emulsifier may be glyceryl stearate/poly(ethylene glycol) (PEG)-100 stearate.

Other emulsifiers that may be used in a composition in accordance with the principles of the present disclosure, in similar percentage ranges to those listed above, include lecithin, cetyl alcohol, cetearyl alcohol, polyglyceryl oleate, methylglucose sesquistearate, POLAWAX, PEG-80 glyceryl cocate, ceteareth-20, and polysorbate 20, among others.

Dimethicone is also known as polydimethylsiloxane (PDMS) and can, in some instances, be considered an emulsifier. In some embodiments, dimethicone may be the only emulsifier. In other embodiments, dimethicone is included and other emulsifiers are incorporated as well. Dimethicone may be present in the composition in an amount of from about 0.01 to about 20.00, of from about 0.02 to about 15.00, of from about 0.05 to about 10.00, of from about 0.10 to about 8.00, of from about 0.20 to about 5.00, of from about 0.25 to about 3.50, of from about 0.50 to about 2.50, of from about 0.50 to about 1.00, or of about 0.60, % by weight based on the total weight of the composition. In various non-limiting embodiments, all values and ranges of values between the aforementioned values are hereby expressly contemplated.

The emulsifier may be a fatty alcohol. Fatty alcohols may be straight- or branched-chain primary alcohols. These alcohols may contain from about 4 to about 26 carbons, inclusive. Examples of fatty alcohols include but are not limited to lauryl, stearyl, and oleyl alcohols. In one embodiment of the present disclosure, a fatty alcohol such as stearyl alcohol (or 1-octadecanol) may be present at about 0.01% to about 10.00%, or more specifically at about 0.50% to about 5.00%, or more specifically at about 1.00% to about 3.00%, or in another embodiment at about 1.80%. In various non-limiting embodiments, all values and ranges of values between the aforementioned values are hereby expressly contemplated.

Other fatty alcohols that may be used in a composition in accordance with the principles of the present disclosure, in similar percentage ranges to those listed above, include cetyl alcohol and cetostearyl alcohol, among others.

In many embodiments, the emulsifier is present in the composition in an amount of from about 0.50% to about 8.00%, or more specifically at about 1.00% to about 7.00%, or more specifically at about 2.00% to about 6.00%, or more specifically at about 3.00% to about 5.00%, or in another embodiment at about 4.50, % by weight based on the total weight of the composition. The amount of the emulsifier may vary outside of the ranges above, but is typically both whole and fractional values within these ranges. Further, it is to be appreciated that more than one emulsifier may be included in the composition, in which case the total amount of all the emulsifiers included is within the above ranges. In various non-limiting embodiments, all values and ranges of values between the aforementioned values are hereby expressly contemplated.

As is set forth above, the composition includes at least one film-forming agent, which may also be referred to as a thickening agent. In one embodiment, the film-forming agent may be a cation-containing film-forming agent. In some embodiments the film-forming agent is cationic.

The film-forming agent typically includes a quaternary ammonium compound. For example, in various embodiments the film-forming agent includes one or more quaternary ammonium compounds selected from polyquaternium compounds 1-47 as designated by International Nomenclature for Cosmetic Ingredients (INCI). In various embodiments, the one or more polyquaternium compounds are present in the composition in an amount of from about 0.01 to about 2.50, of from 0.02 to about 1.50, of from about 0.04 to about 0.80, or about 0.08, % by weight based on the total weight of the composition. In various non-limiting embodiments, all values and ranges of values between the aforementioned values are hereby expressly contemplated.

In one particular embodiment, the film-forming agent is cationic and includes polyquaternium 37 is poly(2-methacryloxyethyltrimethylammonium chloride). Polyquaternium 37 is cationic and belongs to the family of quaternary ammonium compounds, which are polycationic polymers. Of course, while polyquaternium 37 is used some embodiments of the present disclosure, other INCI polyquaternium compounds may be used, such as polyquaternium compounds 1-47, inclusive.

In one particular embodiment, the film-forming agent (or thickening agent) includes a quaternary ammonium compound (as described above), a monoester of propylene glycol and one or more fatty acids, a polyalkylene oxide, and an oil. In various such embodiments, the quaternary ammonium compound is polyquaternium 37. The monoester of propylene glycol and one or more fatty acids may be selected from propylene glycol dicaprylate, propylene glycol dicaprylate/dicaprate, propylene glycol dicocoate, propylene glycol dipelargonate, propylene glycol oleate, propylene glycol dicaprate, propylene glycol diisostearate, propylene glycol dilaurate, and combinations thereof. For example, in some such embodiments, the monoester of propylene glycol and one or more fatty acids is propylene glycol dicaprylate/dicaprate. In various such embodiments, the polyalkylene oxide has a cationic electrical charge character. For example, in some such embodiments, the polyalkylene oxide is cationic and includes ethylene oxide groups and propylene oxide groups in a molar ratio of from about 10:1 to about 1:1, alternatively of from about 8:1 to about 4:1. In various such embodiments, the polyalkylene oxide is PPG-1 trideceth-6. One such film-forming agent that may be included in accordance with the principles of the present disclosure is SALCARE® SC-96, which is commercially available from BASF Corporation.

Other film-forming agents that may be used in a composition in accordance with the principles of the present disclosure, in similar percentage ranges to those listed above, include hydroxyethylcellulose, natrosol, and other compounds.

In many embodiments, the film-forming agent is present in the composition in an amount of from about 0.01 to about 5, of from about 0.05 to about 3, or from about 0.1 to about 2, or from about 0.15 to about 1, or about 0.2, % by weight based on the total weight of the composition. The amount of the film-forming agent may vary outside of the ranges above, but is typically both whole and fractional values within these ranges. Further, it is to be appreciated that more than one film-forming agent may be included in the composition, in which case the total amount of all the film-forming agents included is within the above ranges. In various non-limiting embodiments, all values and ranges of values between the aforementioned values are hereby expressly contemplated.

The composition may also include a humectant. Humectants are compounds that draw water vapor out of the air and in doing so moisturize the skin. One such humectant is glycerin. Other such humectants that may be used in the composition in accordance with the principles of the present disclosure include propylene glycol, triethylene glycol, tripropylene glycol, polypropylene glycols, hexylene glycol, butylene glycol, glyceryl triacetate, urea, and sodium PCA (a proline derivative); nanolipidgels; sugar alcohols including sorbitol, xylitol, and maltitol; polymeric polyols including polydextrose; alpha hydroxyl acids; and *aloe vera* gel.

If present, the humectant may be present in an amount of from about 0.01 to about 50.00, of from 0.05 to about 40.00, of from about 0.10 to about 25.00, of from about 0.15 to about 20.00, of from about 0.20 to about 10.00, of from 0.50 to about 5.00, of from 1.00 to about 3.00, or about 2.00, % by weight based on the total weight of the composition. The amount of the humectant may vary outside of the ranges above, but is typically both whole and fractional values within these ranges. Further, it is to be appreciated that more than one of the humectants may be included in the composition, in which case the total amount of all the humectants included is within the above ranges. In various non-limiting embodiments, all values and ranges of values between the aforementioned values are hereby expressly contemplated.

The composition may also include a preservative. In one embodiment, the preservative includes phenoxyethanol and ethylhexylglycerin. One such preservative that may be included in accordance with the principles of the present disclosure is EUXYL® PE 9010, which is commercially available from Schülke Inc. In another embodiment, another preservative that may be included in accordance with the principles of the present disclosure is MIKROKILL® COS, which is commercially available from Lanza. If present, the preservative may be present in an amount of from about 0.50 to about 1.10, of from about 0.60 to about 1.00, of from about 0.70 to about 0.95, of from about 0.75 to about 0.95, of from about 0.80 to about 0.95, or of from about 0.80 to about 0.90, % by weight based on the total weight of the composition. In one embodiment, the preservative is present at about 0.80% by weight based on the total weight of the composition. In another embodiment, the preservative makes up about 0.90% by weight based on the total weight of the composition. In another embodiment, the preservative makes up about 0.95% by weight based on the total weight of the composition. The amount of the preservative may vary outside of the ranges above, but is typically both whole and fractional values within these ranges. Further, it is to be appreciated that more than one of the preservatives may be included in the composition, in which case the total amount of all the preservatives included is within the above ranges. In various non-limiting embodiments, all values and ranges of values between the aforementioned values are hereby expressly contemplated.

The composition may include a solvent. The solvent may include an aqueous solvent, a non-aqueous solvent, or combinations thereof. In certain embodiments, when the solvent includes an aqueous solvent, the solvent may be water. The water may be distilled water, sterile water, purified water prepared in accordance with United States Pharmacopeia (USP) standards, or any other type of water that is suitable for use in compositions. Water typically makes up the balance of the composition once the other components and their amounts are determined/selected.

In other embodiments, when the solvent is a non-aqueous solvent, the solvent may be an alcohol. Examples of alcohols suitable for the composition include, by way of non-limiting example, ethanol or isopropyl alcohol. Of course, still other solvents are contemplated.

The solvent may be included in the composition in an amount of at least 1% by weight based on the total weight of the composition. In another embodiment, the solvent may be included in the composition an amount of at least about 50% by weight based on the total weight of the composition. In other embodiments, the solvent may be included in the composition in amount of at least about 5, at least about 10, at least about 20, at least about 30, at least about 40, at least about 50, at least about 60, at least about 70, at least about 80, at least about 90, at least about 95, or at least about 99, % by weight based on the total weight of the composition. In still other embodiments, the solvent may be included in the composition in an amount less than about 99, less then about 95, less then about 90, less then about 80, less then about 70, less than about 60, less then about 50, less then about 40, less then about 30, less then about 20, less than about 10, or less than about 5, % by weight based on the total weight of the composition. In still other embodiments, the solvent is included in an amount of from about 40 to about 99, of from about 50 to about 95, of from about 60 to about 90, of from about 65 to about 85, or of from about 75 to about 85, % by weight based on the total weight of the composition. The amount of solvent may vary outside of the ranges above, but is typically both whole and fractional values within these ranges. Further, it is to be appreciated that more than one solvent may be included in the composition, in which case the total amount of all the solvents included is within the above ranges. In various non-limiting embodiments, all values and ranges of values between the aforementioned values are hereby expressly contemplated.

In certain embodiments, when the solvent is water, water may be included in the composition in an amount of at least about 50% by weight based on the total weight of the composition. In another embodiment, water may be included in the composition in an amount of at least about 60% by weight based on the total weight of the composition. In other embodiments, water may be included in the composition in an amount of at least about 65, at least about 70, at least about 75, or at least about 80, % by weight based on the total weight of the composition. In still other embodiments, water may be included in the composition in an amount of from about 50 to about 99, of from about 60 to about 95, of from about 70 to about 90, of from about 75 to about 90, or of from about 80 to about 90, % by weight based on the total weight of the composition. The amount of water may vary outside of the ranges above, but is typically both whole and fractional values within these ranges. Further, it is to be appreciated that more than one type of water may be included in the composition, in which case the total amount of all the types of water included is within the above ranges. In various non-limiting embodiments, all values and ranges of values between the aforementioned values are hereby expressly contemplated.

The composition may also include one or more additives selected from thickeners, surfactants, pH adjusters, odorants, the colorants, stabilizers, skin protectants, and combinations thereof. Many of these additives are described below in reference to the antiseptic product. If included, the additives may be included in the composition in various amounts. In some embodiments, of the additives included may be non-ionic or cationic.

Certain compounds that are included in a composition formulation may perform multiple roles. For instance, a single compound may be considered to be, in non-limiting fashion, both a humectant and an emollient. In another example, a fatty alcohol may be considered to be an emollient, an emulsifier, a co-emulsifier, a film-forming agent, or any combination thereof. One example of a multifunctional compound disclosed herein is, for example, dimethicone, which may function as an emulsifier, a skin conditioning agent, or both.

In one example, the composition formulated for CHG compatibility may include from about 0.50 to about 8.00% by weight glyceryl stearate/PEG-100 stearate, of from about 0.01 to about 10.00, % by weight stearyl alcohol, of from about 0.01 to about 20.00% by weight isopropyl palmitate, of from about 0.01 to about 20.00% by weight caprylic capric triglyceride, about 0.01 to about 20.00% by weight dimethicone, about 0.01 to about 5.00% by weight SALCARE® SC-96, of from about 0.01 to about 50.00% by weight glycerin, of from about 0.50 to about 1.10% by weight EUXYL® RE 9010, and the balance water, or about 10.00 to about 95.00% by weight water—with all % by weight being % by weight based on the total weight of the composition.

In another example, the composition formulated for CHG compatibility may include about 4.50% by weight glyceryl stearate/PEG-100 stearate, about 1.80% by weight stearyl alcohol, about 3.00% by weight isopropyl palmitate, about 3.00% by weight caprylic capric triglyceride, about 0.60% by weight dimethicone, about 0.20% by weight SALCARE® SC-96, about 2.00% glycerin, about 0.80% EUXYL® PE 9010, and the balance water, or about 84.10% by weight water—with all % by weight being % by weight based on the total weight of the composition.

In another example, a composition formulated for CHG compatibility may contain about 4.50% by weight glyceryl stearate/PEG-100 stearate, about 2.30% by weight stearyl alcohol, about 3.00% by weight isopropyl palmitate, about 3.00% by weight caprylic capric triglyceride, about 0.60% by weight dimethicone, about 0.20% by weight SALCARE® SC-96, about 6.40% by weight glycerin, about 1.40% by weight MIKROKILL® COS, and the balance water, or about 77.60% by weight water—with all % by weight being % by weight based on the total weight of the composition.

In another example, a composition formulated for CHG compatibility may contain about 4.50% by weight glyceryl stearate/PEG-100 stearate, about 1.80 to about 2.30% by weight stearyl alcohol, about 3.00% by weight isopropyl palmitate, about 3.00% by weight caprylic capric triglyceride, about 0.60% by weight dimethicone, about 0.20% by weight SALCARE® SC-96, about 2.00 to about 6.40% by weight glycerin, about 0.8 to about 1.40% by weight of a preservative, and the balance water, or about 77.60 to about 84.10% by weight water—with all % by weight being % by weight based on the total weight of the composition.

When a composition is used with a topical antiseptic product comprising an antiseptic agent such as CHG, a composition including anionic compounds may compromise the efficacy of the antiseptic product. As such, the selection of the components included in the composition may account for this characteristic. For example, in embodiments where the antiseptic product includes at least one of the emollient, the emulsifier, the film-forming agent, the humectant, the preservative, and various other additives, each of these components included may be non-ionic or cationic.

In one particular embodiment, the composition includes less than about 10, about 5, about 4, about 3, about 2, about 1, about 0.5, about 0.4, about 0.3, about 0.2, about 0.1, or less than about 0.1, % by weight of an anionic compound based on the total weight of the composition. In one embodiment, the composition is substantially free of anionic compounds. In another embodiment, the composition is free of anionic compounds.

Substantially free as used herein with reference to the components in the composition is generally defined as less than about 2, about 1, about 0.5, about 0.4, about 0.3, about 0.2, about 0.1, or about 0.05, % by weight of the component based on the total weight of the composition.

Some conventional compositions contain anionic compounds. Because the efficacy of chlorhexidine and CHG are in part due to their cationic nature, the presence of anions reduces or negates its activity as an antiseptic. Thus, application of most types of compositions on CHG-treated skin is not advised. However, in some cases, a composition exclusively incorporating ingredients that are not anionic, and therefore selected from, for example, cationic ingredients, nonionic ingredients, and/or amphoteric ingredients that have a net cationic or uncharged character at the pH of the composition, may provide improved compatibility with CHG.

In one particular embodiment, the composition includes less than about 10, about 5, about 4, about 3, about 2, about 1, about 0.5, about 0.4, about 0.3, about 0.2, about 0.1, or less than about 0.1, % by weight of petrolatum based on the total weight of the composition. Alternatively, the composition may be substantially free of petrolatum. In another embodiment, the composition is free of petrolatum.

Petrolatum may be understood to reference liquid, semisolid, or solid forms of natural grade petrolatum, artificial grade petrolatum, white petrolatum, yellow petrolatum, or F.C.C. grade petrolatum, or derivatives thereof. In certain embodiments, petrolatum refers to molecules having alkyl chain lengths of less than 26 carbon atoms. In certain embodiments, petrolatum may be understood to include semicrystalline mixtures of hydrocarbons having from 16 to 32 carbon atoms, and liquid petrolatums including hydrocarbons of from 16 to 20 carbon atoms.

Inclusion of petrolatum in the composition may lead to one or more undesirable sensory properties, including an undesirable feel to customers based on an oily/greasy sensation and a 'tacky' (i.e., slightly adhesive or gummy to touch) feel. Inclusion of petrolatum in the composition may also lead to flammability, a characteristic undesirable in the hospital/medical center environment. Thus, in certain embodiments, the composition is non-flammable.

In one embodiment, the composition may be made using a hot emulsion method. In this case, the aqueous components are combined in a first mixture, and the oil phase components are combined in a second mixture. In one embodiment, the aqueous phase components include water, a humectant, and a preservative, while the oil phase components are an emulsifier, an emollient, and a film-forming agent (or thickening agent). In one embodiment, the aqueous phase components are water, glycerine, and EUXYL® PE9010. In one embodiment, the oil phase components are glyceryl stearate/PEG-100 stearate, stearyl alcohol, isopropyl palmitate, caprylic capric triglyceride, demethicone, and SALCARE® SC-96. The aqueous phase and the oil phase are each heated separately at an elevated temperature between about 75 and about 80° C., inclusive, held at the elevated temperature for a time, in one embodiment the time being about 5 to 15 minutes, cooled, and mixed to form the composition.

Skin is acidic. The term "acid mantle" is used to describe skin pH which is typically from about 4 to about 6. Maintaining skin pH may be important for skin integrity, comfort, and health, and even barrier properties, e.g. antimicrobial defense properties. As such, maintaining skin pH is useful for patient health and comfort.

As is alluded to above, the composition may be used with a topical antiseptic product comprising a cationic antiseptic agent. Because the efficacy of such cationic antiseptic agents (e.g. CHG) are in part due to their cationic nature, the presence of anionic compounds reduces or negates its activity as an antiseptic. To this end, the components of the composition, e.g. the emollient, the emulsifier, and the film-forming agent, etc. have an electrical charge property selected from non-ionic, amphoteric, and cationic. In some embodiments, each of the emollient, the emulsifier, and the film-forming agent have a nonionic electrical charge property. In other embodiments, at least one of the emollient, the emulsifier, and the film-forming agent is cationic. In other words, the composition includes a minimal amount of anionic compounds and is typically acidic so that it maintains the efficacy of the cationic antiseptic agent, e.g. CHG.

Anionic compounds tend to raise the pH of the composition, i.e. decrease the acidity and increase the basicity of the composition, while cationic compounds tend to lower the pH of the composition, i.e. increase the acidity and decrease the basicity of the composition. Since the composition does not include or, at best, includes a minimal amount of anionic compounds, the composition has a pH below 7, i.e., is acidic.

Because skin is acidic and the composition is more effective (with respect to maintaining the efficacy of the antiseptic product) when acidic, the pH of the composition may be important. If the composition lowers skin pH too much, the composition may cause patient discomfort, if the composition increases pH of the skin, it may reduce the efficacy of the antiseptic product. As such, in many embodiments, the composition is carefully formulated to have a pH of between about 3 and about 7, alternatively between about 3 and about 6, or between about 4 and about 6. More specifically, the composition may have a pH of about 3.5 to about 6, about 3.5 to about 5.5, about 3.5 to about 5, about 3.5 to about 4.5, about 3.5 to about 4, about 4 to about 6, about 4 to about 5.5, about 4 to about 5.0, about 4 to about 5.5, about 4 to about 5, about 4 to about 4.5, about 4.5 to about 6, about 4.5 to about 5.5, about 4.5 to about 5.0, about 4.5 to about 6, about 4.5 to about 5.5, about 4.5 to about 5, about 6.5, about 5.5, about 5, about 4.5, about 4, about 3.5, or about 3. In various non-limiting embodiments, all values and ranges of values between the aforementioned values are hereby expressly contemplated.

In one embodiment, the composition consists of nonionic components and water, with a single cationic component or a combination of cationic components present at less than or equal to about 5.00% by weight. In another embodiment, the composition consists of nonionic components and water, with a single cationic component or a combination of cationic components present at less than or equal to about 4.00% by weight. In another embodiment, the composition consists of nonionic components and water, with a single cationic component or a combination of cationic components present at less than or equal to about 3.00% by weight. In another embodiment, the composition consists of nonionic components and water, with a single cationic component or a combination of cationic components present at less than or equal to about 2.50% by weight. In another embodiment, the composition consists of nonionic components and water, with a single cationic component or a combination of cationic components present at less than or equal to about 2.00% by weight. In another embodiment, the composition consists of nonionic components and water, with a single cationic component or a combination of cationic components present at less than or equal to about 1.00% by weight. In another embodiment, the composition consists of nonionic components and water, with a single cationic component or a combination of cationic components present at less than or equal to about 0.80% by weight. In another embodiment, the composition consists of nonionic components and water, with a single cationic component or a combination of cationic components present at less than or equal to about 0.75% by weight. In another embodiment, the composition consists of nonionic components and water, with a single cationic component or a combination of cationic components present at less than or equal to about 0.65% by weight. In another embodiment, the composition consists of nonionic components and water, with a single cationic component or a combination of cationic components present at less than or equal to about 0.50% by weight. In another embodiment, the composition consists of nonionic components and water, with a single cationic component or a combination of cationic components present at less than or equal to about 0.40% by weight. In another embodiment, the composition consists of nonionic components and water, with a single cationic component or a combination of cationic components present at less than or equal to about 0.30% by weight. In another embodiment, the composition consists of nonionic components and water, with a single cationic component or a combination of cationic components present at less than or equal to about 0.25% by weight. In another embodiment, the composition consists of nonionic components and water, with a single cationic component or a combination of cationic components present at less than or equal to about 0.20% by weight. All % by weight above being % by weight based on the total weight of the composition.

In another embodiment, the composition consists of nonionic components and water, with a single cationic component or a combination of cationic components present at less than or equal to about 0.15% by weight. In another embodiment, the composition consists of nonionic components and water, with a single cationic component or a combination of cationic components present at less than or equal to about 0.10% by weight—with all % by weight being % by weight based on the total weight of the composition.

In another embodiment, the composition consists of nonionic components and water, and has a pH between about 3 and about 6, the composition having a stable pH and forming a stable emulsion at room temperature.

The Method:

A method of soothing irritation that does not diminish the efficacy of the antiseptic product is also disclosed. In a typical embodiment, the composition may be applied to a patient's skin to sooth irritation that does not diminish the efficacy of the antiseptic product. As such, the step of applying the composition is typically conducted subsequent to the step of applying the topical antiseptic product.

The method includes the steps of providing the topical antiseptic product and the composition. The composition is just as described above. For example, the composition has a pH of from about 3 to about 6 and includes the emollient, the emulsifier, the film-forming agent, and various combinations of the optional components described above. The antiseptic product is just as described below. The antiseptic product and the composition are just as described below. For example, the antiseptic product includes the cationic antiseptic agent, e.g. CHG, in a concentration of from about 0.5 to about 8% and various combinations of the optional components described above.

The method also includes the step of applying the antiseptic product to a target area on the skin of a patient. The step of applying the antiseptic product to the target area reduces the likelihood of, or prevents, infection, particularly in hospital patients who are to undergo invasive procedures.

The step of applying the antiseptic product to the target area may be conducted via hand, with a cloth, a foam, a brush, a squeeze bottle, etc.

Applicators may be an effective means of applying the antiseptic product to the skin or mucous membranes. For example, among their many uses, applicators may be used to apply the antiseptic product to decolonize the skin or mucous membranes of a patient or a healthcare worker prior to a surgical procedure to help prevent a surgical site infection. In one embodiment, the step of applying the antiseptic product is conducted with an applicator. By way of non-limiting example, suitable examples of the applicator include a cloth, a foam, a brush, a squirt bottle, a roller, etc.

The applicator facilitates topical application of the antiseptic product to the skin or mucous membranes of a patient. As such, the applicator may take any form suitable for topically applying the antiseptic product to the skin or mucous membranes of a patient. Characteristics that may be considered when determining whether an applicator is suitable include, by way of non-limiting example, porosity, absorbency, skin or mucous membrane contactable surface area, biocompatibility, ability of the applicator to retain the antiseptic product, cost of production, etc.

Once the antiseptic product is applied, the method optionally includes the step of drying the antiseptic product on the target area. In other words, the method may further include the step of drying the topical antiseptic product. The topical antiseptic product can be allowed to dry via evaporation, e.g. allowing the antiseptic product to evaporate at ambient temperatures. Of course, heat and air flow can also be used in the step of drying the topical antiseptic product (e.g. a hair dryer or the like can be used to facilitate drying of the antiseptic product in the target area). In other words, the step of drying can further utilize heat and/or air-flow based drying in addition to ambient conditions.

The method also includes the step of applying the composition to the target area. In some embodiments, the step of applying the composition is conducted subsequent to the step of applying the antiseptic product, but prior to the drying of the topical antiseptic product. That is, in some embodiments, the antiseptic product may be applied and not yet dried, or applied and partially dried when the composition is applied to the target area.

The step of applying the composition to the target area may be conducted via hand, with a cloth, a foam, a brush, a squeeze bottle, etc. By way of non-limiting example, suitable examples of the applicator include a cloth, a foam, a brush, a squirt bottle, a roller, etc.

In some embodiments, the step of applying the composition is conducted subsequent to, and less than about 30, less then about 25, less then about less than about 14, less then about 13, less than about 12, less then about 10, less then about 9, less then about 8, less then about 7, less than about 6, less then about 5, greater than about 1, greater than about 2, greater than about 3, greater than about 5, greater than about 5, greater than about 6, greater than about 7, greater than about 8, greater than about 9, greater than about 10, greater than about 15, and greater than about 20, minutes after the step of applying the topical antiseptic product is conducted. In various embodiments, the composition is applied at a time of about 1 to about 25, from about 3 to about 20, from about 5 to about 15, minutes after the step of applying the topical antiseptic product is conducted. In various non-limiting embodiments, all values and ranges of values between the aforementioned values are hereby expressly contemplated.

The Topical Antiseptic Product:

The topical antiseptic product (the antiseptic product) includes a cationic antiseptic agent and, typically, a solvent.

In a typical embodiment, the cationic antiseptic agent ("antiseptic agent") includes chlorhexidine gluconate ("CHG"), a broad-spectrum, persistent antiseptic. CHG is the gluconate or digluconate salt of the antibacterial/antiseptic chlorhexidine. Chlorhexidine is cationic and acts as a bacteriostatic or bacteriocidal compound. The cationic chlorhexidine is attracted to negatively-charged bacterial cell walls and disrupts the membranes of bacteria, slowing their growth or causing cell death. Chlorhexidine is effective against a wide array of microorganisms, including gram-positive bacteria, gram-negative bacteria, and yeasts. When applied to mammalian skin, chlorhexidine remains in place, allowing for its use as a short- and longer-term antiseptic.

That is, the CHG may be free base chlorhexidine or a pharmaceutically acceptable salt of chlorhexidine. When the chlorhexidine is a pharmaceutically acceptable salt of chlorhexidine, the chlorhexidine may be chlorhexidine dihydrochloride, chlorhexidine diacetate, chlorhexidine digluconate (also known as chlorhexidine gluconate, or CHG), chlorhexidine dilactate, chlorhexidine digalactate, or combinations thereof. In certain embodiments, the antiseptic agent is CHG. The pharmaceutically acceptable salt of chlorhexidine may be selected based on the solvent of the antiseptic product due to the solubility properties of the pharmaceutically acceptable salt of chlorhexidine. For instance, CHG is soluble in water whereas chlorhexidine diacetate is substantially insoluble in water and is therefore more suitable for non-aqueous solvents.

It will be appreciated that the cationic antiseptic agent may include compounds other than chlorhexidine such as, by way of non-limiting example, aminoglycoside compounds, polyhexanide, triclosan, quaternary ammonium compounds such as cetrimide, proflavine hemisulphate, chlorocresol, chlorophene, chloroxylenol, iodine, iodophors, etc., and combinations thereof. Of course, still other antiseptic agents are contemplated. Thus, while the term 'chlorhexidine' is used as an adjective throughout this disclosure to describe the product, article and other components thereof, it should be appreciated that products/articles may be free from chlorhexidine components if other antiseptic agents are utilized.

The cationic antiseptic agent may be included in the antiseptic product in an amount of from about 0.1 to about 10% by weight based on the total weight of the antiseptic product. In another embodiment, the antiseptic agent may be included in an amount of from about 0.5 to about 8.0% by weight based on the total weight of the antiseptic product. In yet another embodiment, the cationic antiseptic agent may be included in an amount of from about 1.5 to about 5.0% by weight based on the total weight of the antiseptic product. In other embodiments, the cationic antiseptic agent may be included in an amount from about 0.5 to about 10, of from about 1.0 to about 10, of from about 1.5 to about 10, of from about 2.0 to about 10, of from about 2.5 to about 10, of from about 3.0 to about 10, of from about 3.5 to about 10, of from about 4.0 to about 10, of from about 4.5 to about 10, of from about 5.0 to about 10, of from about 5.5 to about 10, of from about 6.0 to about 10, of from about 6.5 to about 10, of from about 7.0 to about 10, of from about 7.5 to about 10, of from about 8.0 to about 10, of from about 8.5 to about 10, of from about 9.0 to about 10, or of from about 9.5 to about 10, % by weight based on the total weight of the antiseptic product. In still other embodiments, the cationic antiseptic agent may be included in the antiseptic product in an amount of from about 0.1 to about 9.5, of from about 0.1 to about 9.0, of from about 0.1 to about 8.5, of from about 0.1 to about 8.0, of from about 0.1 to about 7.5, of from about 0.1 to about 7.0, of from about 0.1 to about 6.5, of from about 0.1 to about 6.0, of from about 0.1 to about 5.5, of from about 0.1 to about 5.0, of from about 0.1 to about 4.5, of from about 0.1 to about 4.0, of from about 0.1 to about 3.5, of from about 0.1 to about 3.0, of from about 0.1 to about 2.5, of from about 0.1 to about 2.0, of from about 0.1 to about 1.5, of from about 0.1 to about 1.0, or of from about 0.1 to about 0.5, % by weight based on the total weight of the antiseptic product. In still other embodiments, the cationic antiseptic agent may be included in the antiseptic product in an amount of from about 0.5 to about 8.0, of from about 1.0 to about 6.0, of from about 1.5 to about 5.0, of from about 1.8 to about 4.5, of from about 1.8 to about 3.5, or of from about 1.8 to about 2.5, % by weight based on the total weight of the antiseptic product. The amount of the cationic antiseptic agent may vary outside of the ranges above, but is typically both whole and fractional values within these ranges. Further, it is to be appreciated that more than one of the cationic antiseptic agents may be included in the antiseptic product, in which case the total amount of all the antiseptic agents included is within the above ranges.

The antiseptic product typically includes a solvent. The solvent may include an aqueous solvent, a non-aqueous solvent, or combinations thereof. In certain embodiments, when the solvent includes an aqueous solvent, the solvent may be water. The water may be distilled water, sterile water, purified water prepared in accordance with United States Pharmacopeia (USP) standards, or any other type of water that is suitable for use in antiseptic products.

In other embodiments, when the solvent is a non-aqueous solvent, the solvent may be an alcohol. Examples of alcohols suitable for the antiseptic product include, by way of non-limiting example, ethanol or isopropyl alcohol. Of course, still other solvents are contemplated.

The solvent may be included in the antiseptic product in an amount of at least 1% by weight based on the total weight of the antiseptic product. In another embodiment, the solvent may be included in the antiseptic product an amount of at least about 50% by weight based on the total weight of the antiseptic product. In other embodiments, the solvent may be included in the antiseptic product in amount of at least about 5, at least about 10, at least about 20, at least about 30, at least about 40, at least about 50, at least about 60, at least about 70, at least about 80, at least about 90, at least about 95, or at least about 99, % by weight based on the total weight of the antiseptic product. In still other embodiments, the solvent may be included in the antiseptic product in an amount less than about 99, less then about 95, less then about 90, less than about 80, less then about 70, less then about 60, less then about 50, less then about 40, less than about 30, less then about 20, less then about 10, or less than about 5, % by weight based on the total weight of the antiseptic product. In still other embodiments, the solvent is included in an amount of from about 40 to about 99, of from about 50 to about 95, of from about 60 to about 90, of from about 65 to about 85, or of from about 75 to about 85% by weight based on the total weight of the antiseptic product. The amount of solvent may vary outside of the ranges above, but is typically both whole and fractional values within these ranges. Further, it is to be appreciated that more than one solvent may be included in the antiseptic product, in which case the total amount of all the solvents included is within the above ranges.

In certain embodiments, when the solvent is water, water may be included in the antiseptic product in an amount of at least about 50% by weight based on the total weight of the antiseptic product. In another embodiment, water may be included in the antiseptic product in an amount of at least about 60% by weight based on the total weight of the antiseptic product. In other embodiments, water may be included in the antiseptic product in an amount of at least about 65, at least about 70, at least about 75, or at least about 80, % by weight based on the total weight of the antiseptic product. In still other embodiments, water may be included in the antiseptic product in an amount of from about 50 to about 99, of from about 60 to about 95, of from about 70 to about 90, of from about 75 to about 90, or of from about 80 to about 90, % by weight based on the total weight of the antiseptic product. The amount of water may vary outside of the ranges above, but is typically both whole and fractional values within these ranges. Further, it is to be appreciated that more than one type of water may be included in the antiseptic product, in which case the total amount of all the types of water included is within the above ranges.

In some embodiments, at least about 95% of the antiseptic agent is dissolved in the solvent of the antiseptic product. In other embodiments, at least about 50, about 60, about 70, about 80, about 90, about 99, % by weight of the antiseptic agent is dissolved in the solvent of the antiseptic product. It is further contemplated that all of, or substantially all of, the antiseptic agent may be dissolved in the solvent of the antiseptic product.

The antiseptic product may further include a humectant. The humectant may be compatible for use in the antiseptic product, particularly in view of the antiseptic agent included in the antiseptic product. The humectant may be, by way of non-limiting example, glycerol prepared according to USP standards (USP glycerol), propylene glycol, polyethylene glycol, N-methyl pyrrolidone, N-ethyl pyrrolidone, diacetone alcohol, γ-butyryl lactone, ethyl lactate, low molecular weight polyethylene glycol, and combinations thereof. In certain embodiments, the humectant includes USP glycerol and propylene glycol. Of course, other types of humectants are contemplated such as, by way of non-limiting example, monosaccharides, disaccharides, castor oil and derivatives and salts thereof, vegetable oil extracts such as triglycerides, and combinations thereof. Of course, still other humectants are contemplated.

When present, the humectant may be included in the antiseptic product in an amount less than about 20% by weight based on the total weight of the antiseptic product. In another embodiment, the antiseptic product is included in an amount of from about 3.0 to about 10% by weight based on the total weight of the antiseptic product. In other embodiments, the humectant is included in the antiseptic product in an amount less than about 17.5, less then about 15, less than about 12.5, less then about 10, less then about 7.5, less then about 5.0, or less than about 2.5, % by weight based on the total weight of the antiseptic product. In still other embodiments, the humectant is included in an amount of at least about 2.5, at least about 5.0, at least about 7.5, at least about 10, at least about 12.5, at least about 15, at least about 17.5, or at least about 20, % by weight based on the total weight of the antiseptic product. In still other embodiments, the humectant is included in the antiseptic product in an amount of from about 3.5 to about 9.0, of from about 4.0 to about 8.0, of from about 4.5 to about 7.0, or of from about 5.0 to about 6.0, % by weight based on the total weight of the antiseptic product. The amount of humectant may vary outside of the ranges above, but is typically both whole and fractional values within these ranges. Further, it is to be appreciated that more than one humectant may be included in the antiseptic product, in which case the total amount of all the humectants included is within the above ranges. For example, the humectant may include USP glycerol in an amount of from about 2.0 to about 3.0% by weight based on the total weight of the antiseptic product and propylene glycol in an amount of from about 2.5 to about 3.5% by weight based on the total weight of the antiseptic product.

The antiseptic product may further include an emollient. The emollient may be of any type that is suitable for topical application to a patient. The emollient may be, by way of non-limiting example, petroleum-based oils, petrolatum, vegetable oils, mineral oils, lanolin and derivatives thereof, glycerol esters and derivatives thereof, fatty esters, propylene glycol esters and derivatives thereof, alkoxylated carboxylic acids, *aloe vera*, fatty alcohols, dimethicone, alkyl methicones, alkyl dimethicones, phenyl silcones, alkyl trimethylsilanes, and combinations thereof. In certain embodiments, the emollient includes dimethicone and *aloe vera*. Of course, still other emollients are contemplated.

When present, the emollient or other components of the antiseptic product may include insoluble particles. In the context of this disclosure "insoluble particles" are particles that are not soluble in the solvent of the antiseptic product. In one particular embodiment, the antiseptic product further includes water-insoluble particles comprising dimethicone particles having an average diameter of greater than about 0.2 microns.

When present, the emollient may be included in the antiseptic product in an amount less than about 10% by weight based on the total weight of the antiseptic product. In another embodiment, the emollient may be included in the antiseptic product in an amount less than about 5% by weight based on the total weight of the antiseptic product. In other embodiments, the emollient is included in the antiseptic product in an amount less than about 2.5, less than about 2.0, less then about 1.5, less then about 1.0, less then about 0.5, less then about 0.25, or less than about 0.2, % by weight based on the total weight of the antiseptic product. Alternatively, the antiseptic product includes an amount of emollient of from about 0.01 to about 1, about 0.1 to about 0.25, or about 0.1 to about 2, % by weight based on the total weight of the antiseptic product. The amount of emollient may vary outside of the ranges above, but is typically both whole and fractional values within these ranges. Further, it is to be appreciated that more than one emollient may be included in the antiseptic product, in which case the total amount of all the emollients included is within the above ranges.

The antiseptic product may further include a surfactant. The surfactant may be any surfactant that is compatible with the antiseptic agent of the antiseptic product. Depending on the antiseptic agent included in the antiseptic product, the surfactant may be a cationic surfactant, an anionic surfactant, non-ionic surfactant, or combinations thereof. When the surfactant is a non-ionic surfactant, the non-ionic surfactant may be, by way of non-limiting example, polysorbate 20, polysorbate 40, polysorbate 60, polysorbate 80, polysorbate 120, a polyoxyethylene alkyl ether, polyoxyethylene cetyl ether, polyoxyethylene palmityl ether, polyoxyethylene oxide hexadecyl ether, polyethylene glycol cetyl ether, a sucrose ester, a partial ester of sorbitol, a monoglyceride, a diglyceride, di- and tri-esters of sucrose with fatty acid, nonylphenol ethoxylate (Igepal CO 630), nonoxynol-9, and combinations thereof. In certain embodiments, the surfactant includes polysorbate 20 and Igepal CO 630. Of course, still other surfactants are contemplated.

When present, the surfactant may be included in the antiseptic product in an amount less than about 5.0% by weight based on the total weight of the antiseptic product. In another embodiment, the surfactant may be included in the antiseptic product in an amount less than about 2.5% by weight based on the total weight of the antiseptic product. In other embodiments, the surfactant may be included in the antiseptic product in an amount less than about 2.0, less than about 1.5, less then about 1.0, less then about 0.75, less then about 0.50, less than about 0.25, less then about 0.2, less then about 0.15, or less than about 0.1, % by weight based on the total weight of the antiseptic product. Alternatively, the surfactant may be included in the antiseptic product in an amount of from about 0.01 to about 2, about 0.05 to about 1.5, or about 0.01 to about 0.75, % by weight based on the total weight of the antiseptic product. The amount of surfactant may vary outside of the ranges above, but is typically both whole and fractional values within these ranges. Further, it is to be appreciated that more than one surfactant may be included in the antiseptic product, in which case the total amount of all the surfactants included is within the above ranges.

The antiseptic product may further include a pH adjuster. The pH adjuster may be any pH adjuster compatible for use in the antiseptic product. The pH adjuster may be, by way of non-limiting example, adipic acid and derivatives thereof, glycine and derivatives thereof, citric acid and derivatives thereof, calcium hydroxide, magnesium aluminometasilicate, glucono delta lactone, or combinations thereof. In certain embodiments, the pH adjuster is glucono delta lactone. Of course, still other pH adjusters are contemplated.

When present, the pH adjuster may be included in the antiseptic product in an amount less than 5% by weight based on the total weight of the antiseptic product. In another embodiment, the pH adjuster may be included in the antiseptic product in an amount less than about 2.5% by weight based on the total weight of the antiseptic product. In other embodiments, the pH adjuster may be included in the antiseptic product in an amount less than about 2.0, less than about 1.5, less then about 1.0, less then about 0.75, less then about 0.50, less than about 0.25, less then about 0.2, less then about 0.15, or less than about 0.1, % by weight based on the total weight of the antiseptic product. Alternatively, the pH adjuster may be included in the antiseptic product in an amount of from about 0.01 to about 2, about 0.05 to about 1.5, or about 0.05 to about 0.5, % by weight based on the antiseptic product. The amount of pH adjuster may vary outside of the ranges above, but is typically both whole and fractional values within these ranges. Further, it is to be appreciated that more than one pH adjuster may be included in the antiseptic product, in which case the total amount of all the pH adjusters included is within the above ranges.

The antiseptic product may have any pH suitable for the antiseptic product to be used to disinfect the skin or mucous membranes of a patient, particularly in view of the antiseptic agent included in the antiseptic product. In one embodiment, the antiseptic product may have a pH of from about 3 to about 6. In another other embodiment, the antiseptic product may have a pH of from about 4.2 to about 5.2. In still other embodiments, the antiseptic product may have a pH of from about 3 to about 8, of from about 3 to about 7, of from about 3 to about 6, or of from about 3 to about 5. The pH of the antiseptic product may vary outside of the ranges above in specific embodiments, but is typically both whole and fractional values within these ranges.

The antiseptic product may further include an odorant. The odorant may be any odorant suitable for use in the antiseptic product. The odorant may be, by way of non-limiting example, perfumes, fragrances, ethereal oils, essences, scents, and combinations thereof. Of course, still other odorants are contemplated.

When present, the odorant may be included in the antiseptic product in an amount less than about 5% by weight based on the total weight of the antiseptic product. In another embodiment, the odorant may be included in the antiseptic product in an amount less than about 2.5% by weight based on the total weight of the antiseptic product. In other embodiments, the odorant may be included in the antiseptic product in an amount less than about 2.0, less than about 1.5, less then about 1.0, less then about 0.75, less then about 0.50, less then about 0.25, less than about 0.2, less then about 0.15, or less than about 0.1, % by weight based on the total weight of the antiseptic product. Alternatively, the odorant may be included in the antiseptic product in an amount of from about 0.001 to about 2, about 0.005 to about 1.5, or about 0.005 to about 0.5, % by weight based on the total weight of the antiseptic product. The amount of odorant may vary outside of the ranges above, but is typically both whole and fractional values within these ranges. Further, it is to be appreciated that more than one odorant may be included in the antiseptic product, in which case the total amount of all the odorants included is within the above ranges.

The antiseptic product may further include a colorant. The colorant may be any colorant suitable for use in the antiseptic product. The colorant may be a synthetically derived colorant or a naturally derived colorant. The colorant may be, by way of non-limiting example, Brilliant Blue FCF, Fast Green FCF, indigo carmine, carmoisine lake, erythrosine, carmine lake, tartrazine, annatto, colorants produced by converting a naturally derived colorant to an aluminum or calcium salt, and combinations thereof. Of course, still other colorants are contemplated.

When present, the colorant may be included in the antiseptic product in an amount less than about 5% by weight based on the total weight of the antiseptic product. In another embodiment, the colorant may be included in the antiseptic product in an amount less than about 2.5% by weight based on the total weight of the antiseptic product. In other embodiments, the colorant may be included in the antiseptic product in an amount less than about 2.0, less than about 1.5, less then about 1.0, less then about 0.75, less then about 0.50, less then about 0.25, less than about 0.2, less then about 0.15, or less than about 0.1, % by weight based on the total weight of the antiseptic product. Alternatively, the colorant may be included in the antiseptic product in an amount of from about 0.001 to about 2, about 0.005 to about 1.5, or about 0.005 to about 0.5, % by weight based on the total weight of the antiseptic product. The amount of colorant may vary outside of the ranges above, but is typically both whole and fractional values within these ranges. Further, it is to be appreciated that more than one colorant may be included in the antiseptic product, in which case the total amount of all the colorants included is within the above ranges.

The antiseptic product may further include a stabilizer, a skin protectant, a preservative, or combinations thereof. When present, the stabilizer, the skin protectant, and/or the preservative may each be included in the antiseptic product in amounts of less than 5% by weight based on the total weight of the antiseptic product. In another embodiment, the stabilizer, the skin protectant, and/or the preservative may each be included in the antiseptic product in an amount less than about 2.5% by weight based on the total weight of the antiseptic product. In other embodiments, the stabilizer, the skin protectant, and/or the preservative may be each included in the antiseptic product in an amount less than about 2.0, less then about 1.5, less then about 1.0, less than about 0.75, less then about 0.50, less then about 0.25, less than 0.2, less than 0.15, or less than 0.1, % by weight based on the total weight of the antiseptic product. Alternatively, the stabilizer, the skin protectant, and/or the preservative may each be included in the antiseptic product in an amount of from about 0.001 to about 2, about 0.01 to about 1.5, or about 0.01 to about 0.5, % by weight based on the total weight of the antiseptic product. The amount of the stabilizer, the skin protectant, and/or the preservative may vary outside of the ranges above, but is typically both whole and fractional values within these ranges. Further, it is to be appreciated that more than one of the stabilizer, the skin protectant, and/or the preservative may be included in the antiseptic product, in which case the total amount of all the stabilizers, the skin protectants, and/or the preservatives included is within the above ranges.

In some embodiments, the antiseptic product is free of, or substantially free of, an alcohol having a boiling point less than about 90° C. at 1.0 atm. By way of non-limiting example, an alcohol having a boiling point less than about 90° C. at 1.0 atm may be ethanol or isopropyl alcohol. Alternatively, the antiseptic product may include less than about 5.0% by weight alcohol having a boiling point less than about 90° C. at 1.0 atm based on the total weight of the antiseptic product. Alternatively still, the antiseptic product includes less than about 4.0% by weight, less then about 3.0% by weight, less than about 2.0% by weight, or less than about 1.0% by weight, of alcohol having a boiling point less than about 90° C. at 1.0 atm, each based on the total weight of the antiseptic product. In these embodiments, the antiseptic product is particularly suitable for disinfection of the skin or mucous membranes of a patient because the antiseptic product does not dry the skin or mucous membranes of the patient. Moreover, the antiseptic product may be applied to the skin or mucous membranes of a patient multiple times within a 24 hour period without concern for irritating the skin or mucous membranes of the patient due to dryness. However, despite the fact that an alcohol having a boiling point less than about 90° C. at 1.0 atm is generally not necessary, in certain embodiments, the antiseptic product may include an alcohol having a boiling point less than about 90° C. at 1.0 atm in an amount of from about 5 to about 15% by weight based on the total weight of the antiseptic product.

In one particular embodiment, the antiseptic product includes less than about 10, about 5, about 4, about 3, about 2, about 1, about 0.5, about 0.4, about 0.3, about 0.2, about 0.1, or less than about 0.1, % by weight of alcohol based on the total weight of the antiseptic product. Alternatively, the antiseptic product is substantially free of alcohol. In another embodiment, the antiseptic product is free of alcohol.

Substantially free as used herein with reference to the components in the antiseptic product is generally defined as less than about 2, about 1, about 0.5, about 0.4, about 0.3, about 0.2, about 0.1, or about 0.05, % by weight of the antiseptic product based on the total weight of the antiseptic product. The antiseptic product may include less than about 10, less then about 7.5, less then about 5.0, less then about 2.5, less then about 1.0, or less than about 0.5% by weight of an alcohol based on the total weight of the antiseptic product % by weight of an alcohol based on the total weight of the antiseptic product. Alternatively, the antiseptic product includes no amount of an alcohol. In these embodiments, the antiseptic product is particularly suitable for disinfection of the skin or mucous membranes of a patient because the antiseptic product does not dry the skin or mucous membranes of the patient. Of course, it will be appreciated that in some embodiments, alcohol may be included in the antiseptic product in amounts greater than about 10% by weight based on the total weight of the antiseptic product.

In one particular embodiment, the antiseptic product includes water in an amount of at least about 50% by weight based on the total weight of the antiseptic product and chlorhexidine gluconate (CHG) in an amount of from about 1.5 to about 5.0% by weight based on the total weight of the antiseptic product. The CHG is dissolved in the water. In another embodiment, the antiseptic product consists essentially of water in an amount of at least about 50% by weight based on the total weight of the antiseptic product, chlorhexidine gluconate (CHG) in an amount of from about 1.5 to about 5.0% by weight based on the total weight of the antiseptic product, a humectant in an amount of from about 3.0 to about 10% by weight based on the total weight of the antiseptic product, an emollient in an amount less than about 1.0% by weight based on the total weight of the antiseptic product, and optionally additives selected from the group consisting of a solvent, an antiseptic agent, a humectant, an emollient, a surfactant, a pH adjuster, an odorant, a colorant, or combinations thereof.

In various embodiments, the antiseptic product is, includes, or consists essentially of an antiseptic agent and a solvent. For example, in embodiments that "consist essentially of" the aforementioned components, the antiseptic product may be free of the humectant, the emollient, the surfactant, the pH adjuster, the odorant, the colorant, the stabilizer, the skin protectant, the preservative, and/or combinations thereof. Alternatively, any one or more of these components may be included in an amount less than about 25, about 20, about 15, about 10, about 5, about 4, about 3, about 2, about 1, about 0.1, about 0.05, about 0.01, etc., % by weight or any range thereof, based on a total weight of the antiseptic product. In various non-limiting embodiments, all values and ranges of values between the aforementioned values are hereby expressly contemplated.

In one particular embodiment, the antiseptic product includes less than about 10, about 5, about 3, about 1, about 0.5, or about 0.1, % by weight of an anionic compound based on the total weight of the antiseptic product. For configurations where the antiseptic agent includes CHG, anionic compounds may compromise the efficacy of the antiseptic product. As such, the selection of the components included in the antiseptic product may account for this characteristic. For example, in embodiments where the antiseptic product includes at least one of the humectant, the emollient, the surfactant, the pH adjuster, the odorant, the colorant, the stabilizer, the preservative, and/or the skin protectant, each of these components included may be non-ionic or cationic. In still further embodiments, the antiseptic product may be free of an anionic compound other than the anionic compound(s) included as the antiseptic agent. In other words, no anionic compound may be included in the antiseptic product, other than those anionic compounds of the antiseptic agent.

Many compositions, by contrast, contain anionic compounds. Because the efficacy of chlorhexidine and CHG are in part due to their cationic nature, the presence of anions reduces or negates their activity as an antiseptic. Thus, application of most types of composition to CHG-treated skin is not advised. However, a composition exclusively incorporating ingredients that are not anionic, and therefore selected from, for example, cationic ingredients, nonionic ingredients, and/or amphoteric ingredients that have a net cationic or uncharged character at the pH of the composition.

All combinations of the aforementioned embodiments throughout the entire disclosure are hereby expressly contemplated in one or more non-limiting embodiments even if such a disclosure is not described verbatim in a single paragraph or section above. In other words, an expressly contemplated embodiment may include any one or more elements described above selected and combined from any portion of the disclosure.

It is also to be understood that any ranges and subranges relied upon in describing various embodiments of the present disclosure independently and collectively fall within the scope of the appended claims, and are understood to describe and contemplate all ranges including whole and/or fractional values therein, even if such values are not expressly written herein. One of skill in the art readily recognizes that the enumerated ranges and subranges sufficiently describe and enable various embodiments of the present disclosure, and such ranges and subranges may be further delineated into relevant halves, thirds, quarters, fifths, and so on. As just one example, a range "of from 0.1 to 0.9" may be further delineated into a lower third, i.e. from 0.1 to 0.3, a middle third, i.e. from 0.4 to 0.6, and an upper third, i.e. from 0.7 to 0.9, which individually and collectively are within the scope of the appended claims, and may be relied upon individually and/or collectively and provide adequate support for specific embodiments within the scope of the appended claims. In addition, with respect to the language which defines or modifies a range, such as "at least," "greater than," "less than," "no more than," and the like, it is to be understood that such language includes subranges and/or an upper or lower limit. As another example, a range of "at least 10" inherently includes a subrange of from at least 10 to 35, a subrange of from at least 10 to 25, a subrange of from 25 to 35, and so on, and each subrange may be relied upon individually and/or collectively and provides adequate support for specific embodiments within the scope of the appended claims. Finally, an individual number within a disclosed range may be relied upon and provides adequate support for specific embodiments within the scope of the appended claims. For example, a range "of from 1 to 9" includes various individual integers, such as 3, as well as individual numbers including a decimal point (or fraction), such as 4.1, which may be relied upon and provide adequate support for specific embodiments within the scope of the appended claims.

Several embodiments have been discussed in the foregoing description. However, the embodiments discussed herein are not intended to be exhaustive or limit the invention to any particular form. The terminology which has been used is intended to be in the nature of words of description rather than of limitation. Many modifications and variations are possible in light of the above teachings and the invention may be practiced otherwise than as specifically described.

What is claimed is:

1. A method of soothing an irritation that does not diminish the efficacy of a topical antiseptic product, said method comprising:
   providing a topical antiseptic product comprising chlorhexidine gluconate in a concentration of from about 0.5 to about 8% by weight based on the total weight of the topical antiseptic product and comprising less than about 0.5% by weight, of alcohol, based on the total weight of the antiseptic product;
   providing a composition that comprises an emollient, an emulsifier, and a film-forming agent,
      the composition having a pH of from about 3 to about 6,
      the emollient, the emulsifier, and the film-forming agent each independently having an electrical charge property selected from non-ionic, amphoteric, and cationic, and
      the composition is free of an anionic compound;
   applying the topical antiseptic product to a target area on a skin of a person with a cloth applicator to coat the target area with chlorhexidine gluconate; and
   applying the composition to the coated target area.

2. The method as set forth in claim 1 wherein the topical antiseptic product is free of alcohol.

3. The method as set forth in claim 1 further comprising the step of drying the topical antiseptic product.

4. The method as set forth in claim 3 wherein the step of applying the composition is conducted subsequent to the step of applying the topical antiseptic product, but prior to the drying of the topical antiseptic product.

5. The method as set forth in claim 4 wherein the step of applying the composition is conducted subsequent to, and less than about 3 minutes after, the step of applying the topical antiseptic product.

6. The method as set forth in claim 1 wherein the composition is substantially free of petrolatum.

7. The method as set forth in claim 1 wherein at least one of the emollient, the emulsifier, and the film-forming agent is cationic.

8. The method as set forth in claim 1 wherein the film-forming agent is cationic.

* * * * *

UNITED STATES PATENT AND TRADEMARK OFFICE
CERTIFICATE OF CORRECTION

PATENT NO. : 10,124,067 B2
APPLICATION NO. : 15/486920
DATED : November 13, 2018
INVENTOR(S) : Jodi M. Balbinot et al.

Page 1 of 1

It is certified that error appears in the above-identified patent and that said Letters Patent is hereby corrected as shown below:

In the Claims

Column 22, Line 34 (Claim 5): delete "3" and insert therefor --15--.

Signed and Sealed this
Fifth Day of March, 2019

Andrei Iancu
*Director of the United States Patent and Trademark Office*